(12) United States Patent
Geitz

(10) Patent No.: US 6,576,005 B1
(45) Date of Patent: Jun. 10, 2003

(54) STENT DEPLOYMENT DEVICE AND METHOD FOR DEPLOYING A STENT

(75) Inventor: Kurt Geitz, Sudbury, MA (US)

(73) Assignee: Boston Scientific Corporation, Natick, MA (US)

( * ) Notice: Subject to any disclaimer, the term of this patent is extended or adjusted under 35 U.S.C. 154(b) by 272 days.

(21) Appl. No.: 09/671,586

(22) Filed: Sep. 28, 2000

Related U.S. Application Data

(62) Division of application No. 09/064,738, filed on Apr. 23, 1998, now Pat. No. 6,146,389.

(51) Int. Cl.[7] .................................................. A61F 2/06
(52) U.S. Cl. ...................... 623/1.11; 600/101; 600/129
(58) Field of Search ................................. 600/101, 104, 600/121, 123–125, 127, 129; 604/160; 606/108, 191, 194, 198, 195; 623/1.11, 1.12, 1.27

(56) References Cited

U.S. PATENT DOCUMENTS

| 5,026,377 | A |   | 6/1991  | Burton et al. .............. 606/108 |
| 5,160,341 | A |   | 11/1992 | Brenneman et al. ........ 606/198 |
| 5,257,617 | A |   | 11/1993 | Takahashi |
| 5,372,600 | A |   | 12/1994 | Beyer et al. ............... 606/108 |
| 5,443,454 | A |   | 8/1995  | Tanabe et al. ............. 604/264 |
| 5,443,500 | A | * | 8/1995  | Sigwart ..................... 623/1.17 |
| 5,484,444 | A |   | 1/1996  | Braunschweiler et al. .. 606/108 |
| 5,534,007 | A |   | 7/1996  | St. Germain et al. ....... 606/108 |
| 5,571,168 | A |   | 11/1996 | Toro ............................. 623/1 |
| 5,603,698 | A |   | 2/1997  | Roberts et al. ............. 604/104 |
| 5,723,003 | A | * | 3/1998  | Winston et al. ............ 623/1.13 |
| 5,746,694 | A |   | 5/1998  | Wilk et al. .................. 600/123 |
| 5,782,855 | A |   | 7/1998  | Lau et al. ................... 606/194 |
| 5,800,521 | A | * | 9/1998  | Orth .......................... 623/1.23 |
| 5,891,154 | A |   | 4/1999  | Loeffler ..................... 606/108 |
| 5,928,248 | A |   | 7/1999  | Acker ........................ 606/108 |
| 5,968,052 | A |   | 10/1999 | Sullivan, III et al. ....... 606/108 |
| 5,980,531 | A |   | 11/1999 | Goodin et al. .............. 606/108 |
| 5,984,964 | A |   | 11/1999 | Roberts et al. |
| 5,993,460 | A |   | 11/1999 | Beitelia et al. ............. 606/108 |
| 6,004,328 | A |   | 12/1999 | Solar ......................... 606/108 |
| 6,019,787 | A | * | 2/2000  | Richard et al. ............. 606/194 |
| 6,254,627 | B1| * | 7/2001  | Freidberg .................. 623/1.11 |

FOREIGN PATENT DOCUMENTS

| EP | 0 364 420 |   | 4/1990 |
| EP | 0637454   | * | 2/1995 |
| WO | 96/12436  |   | 5/1996 |
| WO | 97/48343  |   | 12/1997 |
| WO | 98/11846  |   | 3/1998 |

* cited by examiner

Primary Examiner—Kevin Shaver
Assistant Examiner—Michael B. Priddy
(74) Attorney, Agent, or Firm—Finnegan, Henderson, Farabow, Garrett & Dunner, L.L.P.

(57) ABSTRACT

A stent deployment device for deploying a stent within a body cavity comprises an endoscope having a protective cap, a flexible stent, a sheath, and a flexible, elongated member. The protective cap is mounted on the distal end of the endoscope providing a protected surface for retaining the stent. The flexible stent is circumferentially compressed over the perimeter of the cap, and the sheath is then releasably wrapped around the stent to hold it in a compressed configuration over the cap. The flexible, elongated member, such as a wire extending through a working channel of the endoscope, is attached to either the sheath directly or to a releasing device for the sheath. After the endoscopic device is inserted in a body cavity, the flexible, elongated member is pulled through the working channel to release the sheath and deploy the stent into a desired body opening in the body cavity. After deployment of the stent, the sheath can be left in the body cavity for subsequent retrieval or retracted through the endoscopic device.

16 Claims, 4 Drawing Sheets

STENT DEPLOYMENT DEVICE AND METHOD FOR DEPLOYING A STENT

This is a division of application Ser. No. 09/064,738, filed Apr. 23, 1998, now U.S. Pat. No. 6,146,389, which is incorporated herein by reference.

BACKGROUND OF THE INVENTION

The present invention relates to stent deployment devices and methods for deploying stents. More particularly, the present invention concerns a stent deployment device and a method for deploying a stent within the alimentary tract using an endoscope.

Endoscopes are effective devices for diagnosing and treating patients with minimal intervention and discomfort and are often used to explore and perform biopsies in such areas as the alimentary tract. In general, an endoscope has a flexible elongated tubular body equipped with a miniature television camera or other viewing device, a light, and a working lumen or channel. The working channel is used to store and deploy a variety of surgical tools for different endoscopic operations.

A stent is a resilient device often used in anchoring vascular grafts and for supporting body openings during the grafting of vessels and tubes of the body during surgery. Also, stents are frequently used, without grafts, for supporting lumenal patency. More recently, artificial (woven or nonwoven polymeric) grafts are used in cardiac, vascular and nonvascular applications to provide extra support. Moreover, stents can be separated into self expanding and plastically deformed stents. A self expanding stent is deployed by its self expanding resilience. A plastically deformed stent is deployed by plastic deformation of the constituent material with a balloon or other such dilating instrument.

Endoscopes are effectively utilized to deploy stents within a body cavity in a minimally invasive manner. In a conventional method, a stent is compressed to fit into the working channel of the endoscope and is delivered to the body cavity to be treated. However, storing a stent within the working channel of an endoscope causes several problems. First, there is a limitation on the size of the stent that can be compressed to fit in the working channel. Because the working channel of the endoscope is often relatively small, a large stent may not fit within the working channel. Thus, this method is not suitable for deploying large stents.

Additionally, fitting a stent in the working channel often results in extreme deformation of the stent when it is deployed to the body cavity. Since stents are made of resilient material, compression within the working channel can cause the stent to become deformed and fail to return to its original shape if strained beyond a certain point. The more the stent gets strained, the more extreme the deformation is likely to be.

Consequently, there is a need for stent deployment systems and methods that provide a solution to aforementioned problems and permit deployment of stents, regardless of size, into body cavities.

SUMMARY OF THE INVENTION

In accordance with the present invention, as embodied and broadly described herein, the present invention utilizes an endoscope having a distal end and a working channel. A protective cap is mounted on the distal end of the endoscope. A flexible stent is circumferentially compressed over the perimeter of the protective cap. A sheath is releasably wrapped around the stent to hold it in its compressed configuration over the cap. One end of a flexible, elongated member, such as a wire or other flexible member, is attached to the sheath to permit removal from the cap and stent and deployment of the stent in substantially linear transverse alignment within a body cavity. The elongated member extends through the working channel of the endoscope and exits from the distal end thereof.

In accordance with another aspect of the present invention, the stent deployment device comprises one end of a flexible, elongated member attached to a release device for removing a sheath from a cap and deploying the stent in substantially linear transverse alignment within a body cavity.

In yet another aspect of the present invention, the stent deployment device comprises a protective cap adapted for mounting on the distal end of an endoscope with a sheath that is releasably wrapped around the stent to hold the stent in a compressed configuration over the cap. One end of a flexible, elongated member is attached to the sheath to permit its release and deployment in substantially linear transverse alignment within a body cavity by withdrawing the elongated member extending through the working channel of the endoscope, the elongated member exiting from the distal end of the endoscope.

In still another aspect of the present invention, one end of a flexible, elongated member extending through the working channel is attached to a release device for removing a sheath from a cap and deploying a stent in substantially linear transverse alignment within a body cavity by withdrawing the elongated member.

The present invention further comprises a method including the steps of mounting a protective cap on a distal end of an endoscope, compressing a stent circumferentially over the perimeter of the protective cap, releasably wrapping a sheath around the stent to hold the stent in a compressed configuration over the protective cap and withdrawing the flexible, elongated member engaged with the sheath through the endoscope to release the sheath from the protective cap, thereby causing the stent to deploy.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENT(S)

Reference will now be made in detail to the present preferred embodiments of the present invention, examples of which are illustrated in the accompanying drawings. Wherever possible, the same reference numbers will be used throughout the drawings to refer to the same or like parts.

In accordance with the present invention, the stent deployment device is used with an endoscope, and includes a protective cap, a flexible stent, a sheath, and a flexible, elongated member connected to the sheath, such as a wire or other flexible member. The devices and methods of the present invention enable deployment of a stent in substantially linear transverse alignment within a body cavity.

Figure 1:
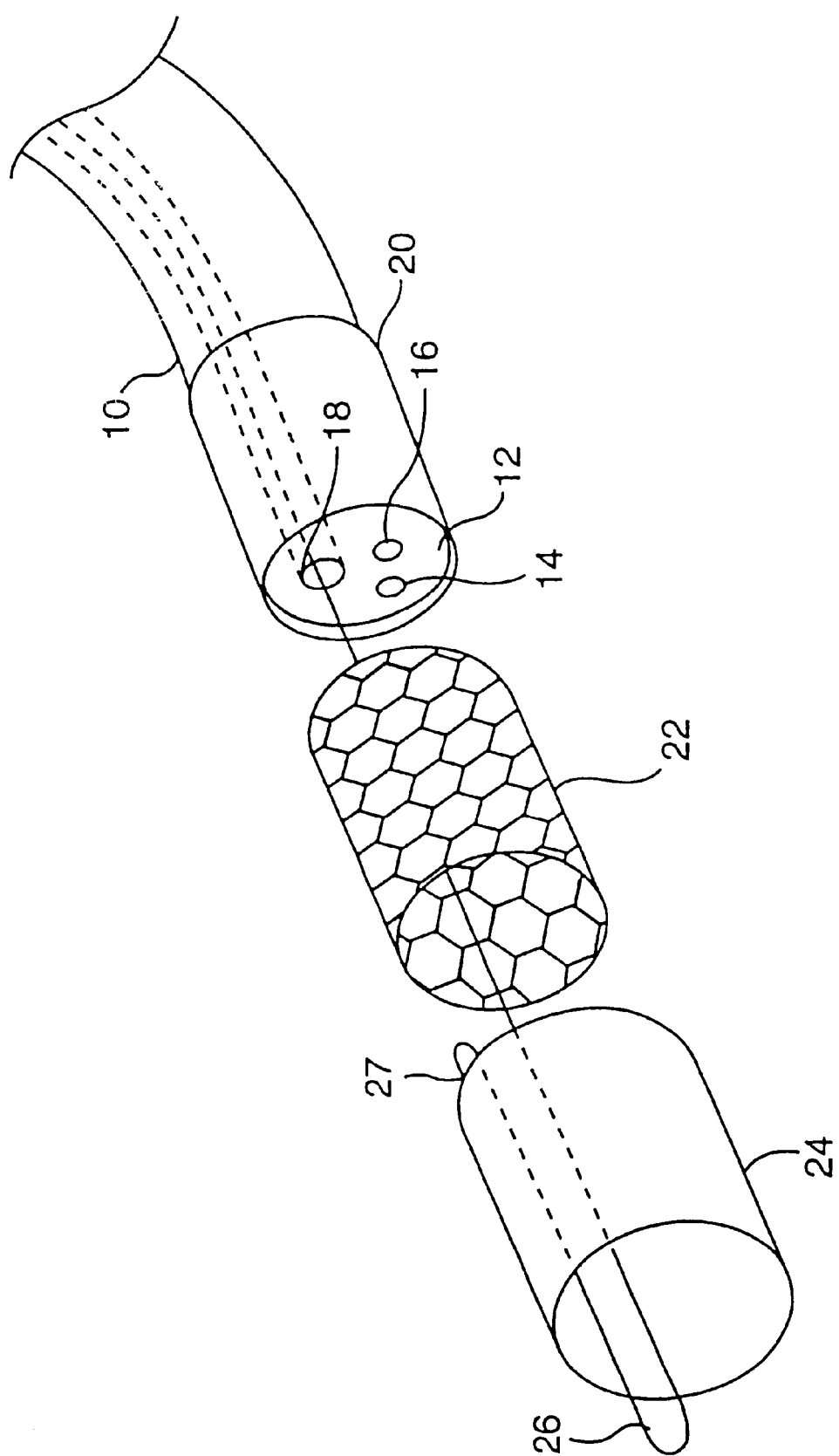
FIG. 1 is an exploded view of a first embodiment of the stent deployment device according to the present invention.
Figure 2:
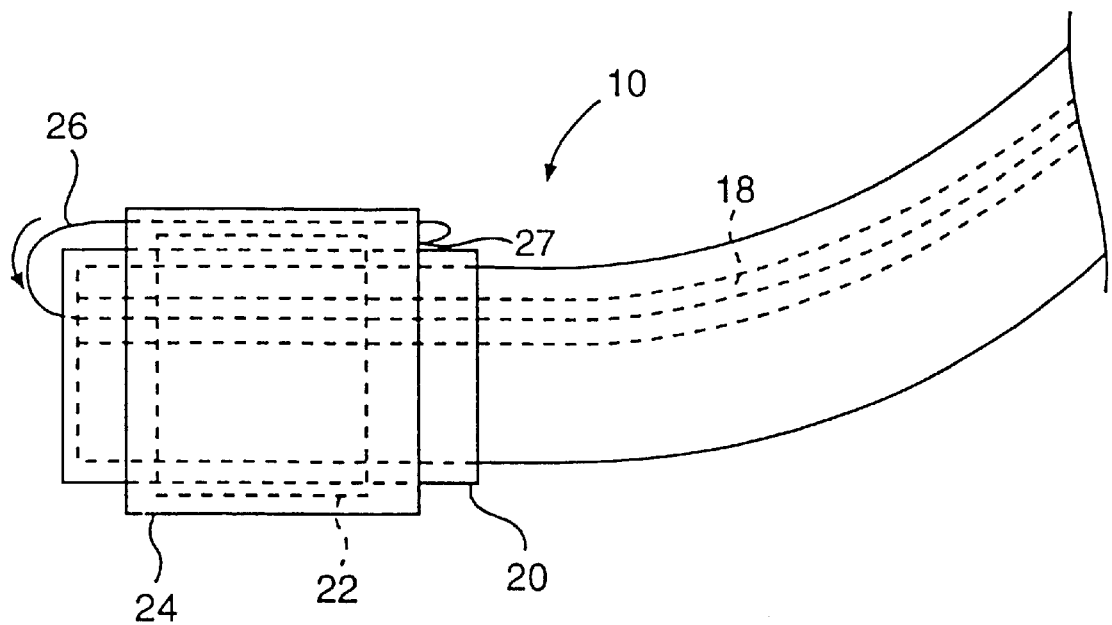
FIG. 2 is a non-exploded side view of the stent deployment device illustrated in FIG. 1.

In a first preferred embodiment of the present invention, illustrated in FIGS. 1 and 2, an endoscope 10 has a flexible elongated tubular body with a distal end 12 for insertion into a body cavity. Generally, endoscope 10 is equipped with an illumination device 14, a viewing device 16, and a working lumen or channel 18. The illumination device 14 provides light for the operation of the endoscope in a dark body cavity. The viewing device 16, which may be a TV camera, captures images in the body cavity, and the images are electrically or optically transmitted through the tubular body of endoscope 10. The working channel 18 extends through the tubular body to the distal end 12 of endoscope 10. The working channel 18 is designed to accommodate various medical instruments, which can include a stent.

As shown in FIGS. 1 and 2, the endoscope 10 has a protective cap 20 mounted onto its distal end 12. The protective cap 20 provides a base surface for retaining stent 22 and protects the body of the endoscope 10 from any abrasion by the stent deployment. Preferably, the protective cap 20 is made of silicone or other elastomers, such as polyurethane, latex and certain nylons, and has a tubular shape. The protective cap 20 may be mounted at the distal end 12 by gripping onto the circumference of the distal end 12. Also, the protective cap 20 may be clipped onto the distal end 12.

The stent 22 is a flexible device preferably made of a resilient material, and substantially returns to its original shape in the absence of any restraint. Materials suitable for the stent include nickel-titanium alloy (Nitinol), medical grade stainless steels, tantalum and other biocompatible metals. Also, certain polymers may be suitable for the stent although some polymers do not have changeable diameters. The stent 22 is circumferentially wrapped and compressed around and over the perimeter of the cap 20. This configuration allows the stent to be retained outside of the endoscope 10 rather than inside. Preferably, the stent 22 has a compressed diameter of approximately 1.0 cm.

A sheath 24 is wrapped around the stent 22 to hold it in a compressed configuration over the cap 20. Once the sheath 24 is removed from cap 20 and the stent 22 in the body cavity, stent 22 deploys within the body cavity in substantially its original shape in order to effectively support the body cavity. The sheath 24 is preferably a thin strip made of Teflon, polyethylene, or any other appropriate material safe to the body, such as polymer films, polyimide, and nylons. In accordance with a first embodiment of the present invention, as illustrated in FIGS. 1 and 2, the sheath 24 can be a sheet that is wrapped around the endoscope 10 body into a tubular shape. The sheath 24 also can have a seamless tubular shape. The sheath 24 holds stent 22 in a compressed form and stays wrapped around the stent 22 due to friction between the sheath 24 and stent 22 surfaces. The length of the sheath 24 largely depends on the length of the stent 22, but the sheath is preferably longer than the stent 22. For example, sheath 24 is preferably about 10 cm. long for retaining a 6 cm. stent 22. As the stent becomes longer in circumference, the relevant length is a bound down stent length when the diameter of the stent is constrained.

A flexible, elongated member 26 extends though the working channel 18 of endoscope 10 and is attached to sheath 24 at connection point 27 for removal of the sheath 24. The elongated member 26 is preferably a pull-wire extending through the working channel 18 of the endoscope 10. In the embodiment shown in FIGS. 1 and 2, the elongated member 26 can be permanently attached to a part of the sheath if at point 27 and remains attached to sheath 24 after it is removed from the cap 20 and the stent 22.

The sheath 24, wrapped around the protective cap 20 and the stent 22, is released by pulling the elongated member 26 in the direction shown in FIG. 2. As shown in FIGS. 1 and 2, the elongated member 26 extends between the sheath 24 and the stent 22 when it is pulled to release the sheath 24. When the elongated member 26 is pulled in the direction shown in FIG. 2, the sheath 24 extends away from distal end 12. Sheath 24 is then drawn through the working channel 18. This configuration is preferable because then the sheath 24 is not left in the body cavity, thus eliminating any need to later retrieve it. After sheath 24 is removed, the stent 22 is free to deploy and will extend in a substantially traverse direction in the body cavity.

Figure 3:
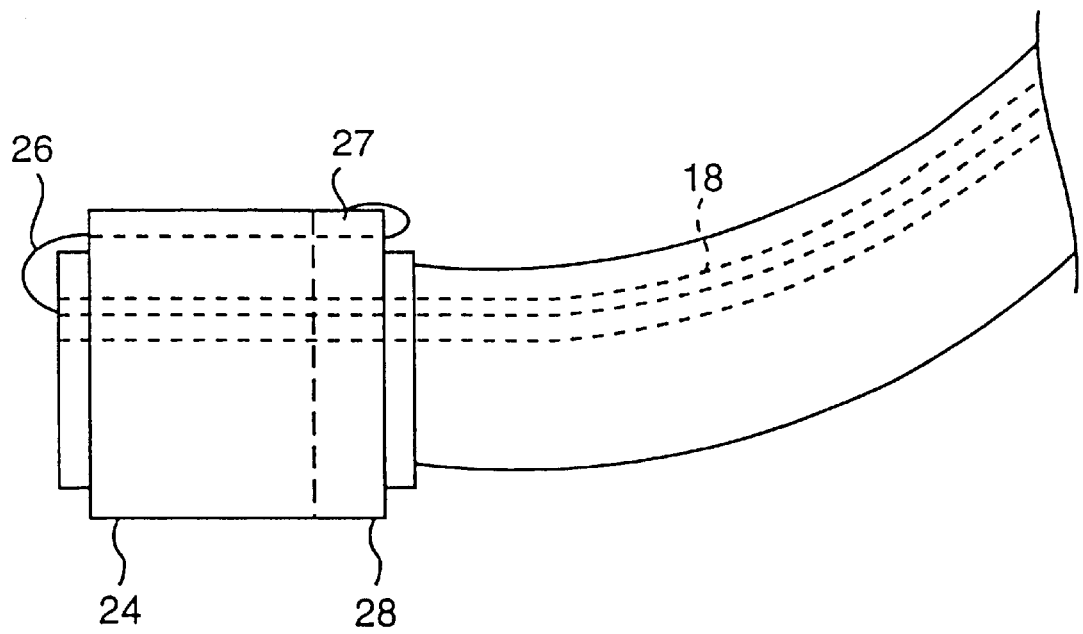
FIG. 3 is a side view of a second embodiment of a stent deployment device in accordance with the present invention.

A second preferred embodiment of the present invention, illustrated in FIG. 3, has a perforated portion 28 along the sheath 24. Elongated member 26 is attached to perforated portion 28 at point 27. Perforated portion 28 is tom away from the remainder of sheath 24 when the elongated member 26 is pulled through the working channel 18, thus releasing the sheath 24 and deploying the stent 22. The sheath 24, with the exception of the perforated portion 28, is left in the body cavity. It may be preferable to leave the sheath 24 within the body cavity if extracting the endoscope 10 with the sheath 24 would likely result in damage to the body cavity, such as small intestines. The portion of sheath 24 left in the body cavity is subsequently retrieved by another endoscopic device extended through working channel 18.

Figure 4:
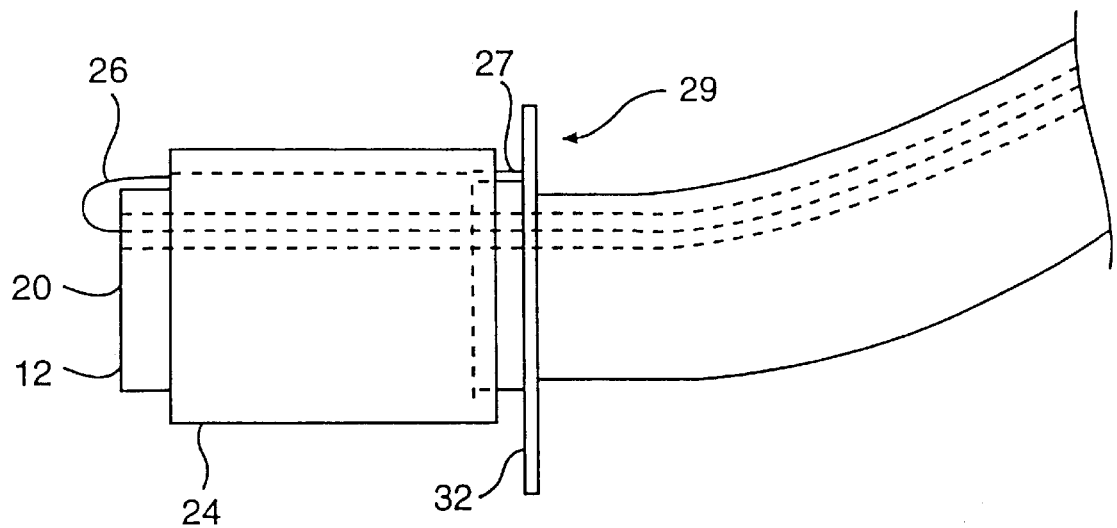
FIG. 4 is a side view of a third embodiment of a stent deployment device in accordance with the present invention.

FIG. 4 illustrates a third preferred embodiment of a stent employment device of present invention. The elongated member 26 is attached to a release device 29 at point 27, which preferably comprises a ring 30 having a flanged portion 32 for removing the sheath 24. The ring 30 is preferably made of biocompatible metal, such as stainless steel or an engineering plastic like acetal. As the elongated member 26 is pulled through the working channel 18, the ring 30 begins to slide to the distal end 12 of the endoscope 10 over the cap 20 and the stent (not shown in the FIG. 4). The flanged portion 32 engages with the sheath 24 and pushes the sheath 24 from the cap 20 and the stent as the ring 30 slides toward the distal end 12 of the endoscope 10, thus releasing the sheath 24, and deploying the stent into the body cavity. The ring 30 can either stay on the cap or completely off the cap after the operation. However, the ring 30 preferably stays on the cap in order to facilitate the removal of the endoscope from the body cavity.

Figure 5:
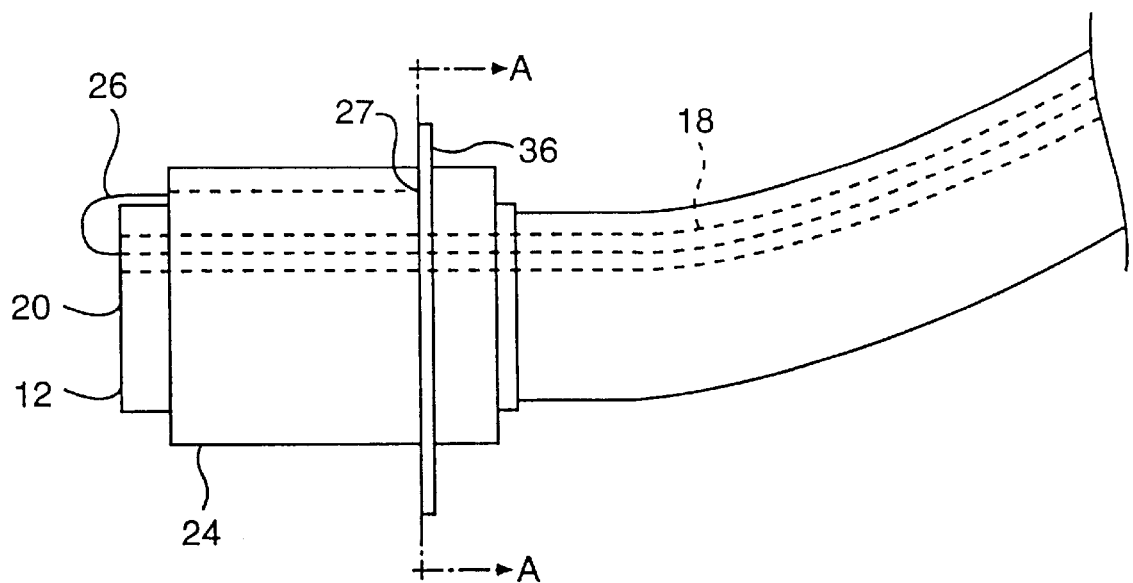
FIG. 5 is a side view of a fourth embodiment of a stent deployment device in accordance with the present invention.
Figure 6:
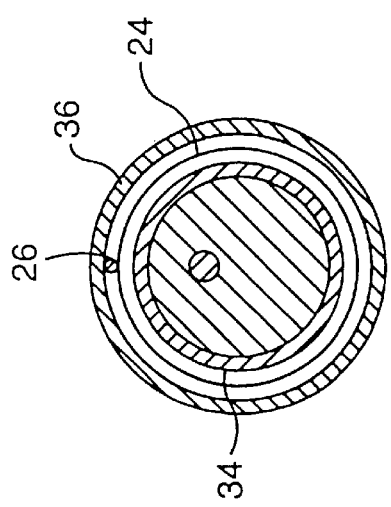
FIG. 6 is a cross-sectional view along line A—A of FIG. 5.

In a fourth preferred embodiment of the present invention, as shown in FIGS. 5 and 6, the elongated member 26 is attached at point 27 to a release device comprising an inner ring 34 and an outer ring 36 concentrically arranged over the cap 20 and the stent (not shown in FIGS. 5 and 6). In this configuration, the sheath 24 and one end of the elongated member 26 are compressed by the inner ring 34 and the outer ring 36. The rings 34 and 36 are preferably made of steel or a ductile metal such as tantalum. Preferably, the outer ring 36 is a swage ring for compressing the sheath 24 and the elongated member 26. When the elongated member 26 is pulled through the working channel 18, the inner ring 34, together with the sheath 24, the elongated member 26 and the outer ring 36, slide over the cap 20 and the stent toward the distal end 12, thus releasing the sheath 24 from the cap and deploying the stent. The rings preferably fall off the cap after the sheath is released.

Figure 7:
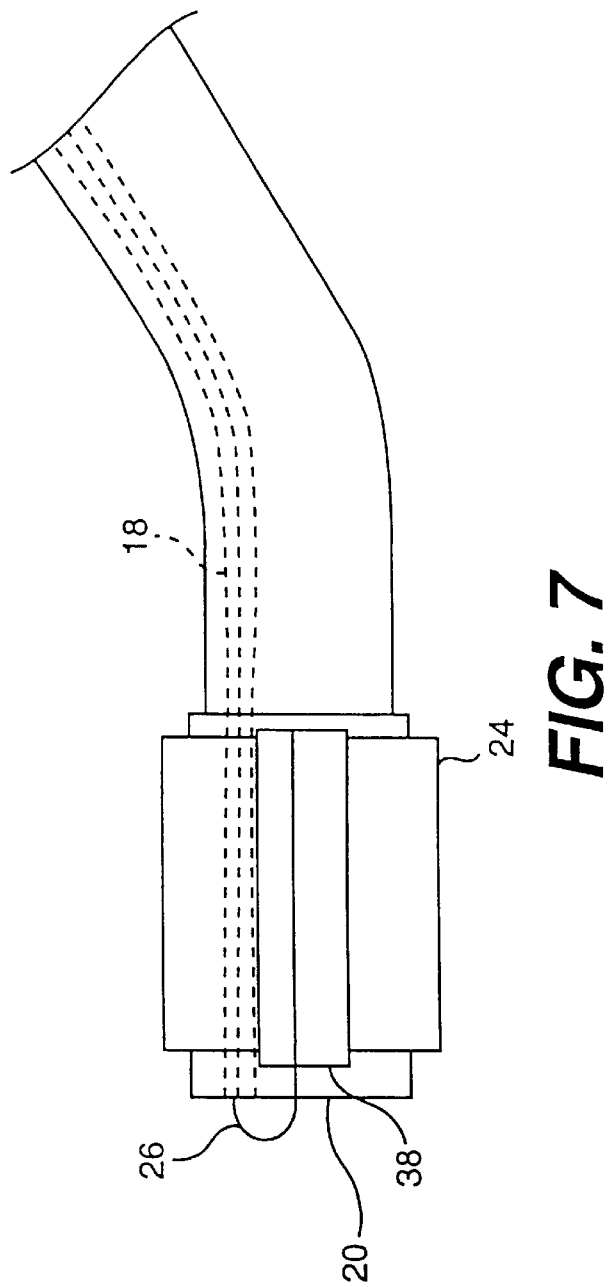
FIG. 7 is a side view of a fifth embodiment of a stent deployment device in accordance with the present invention.

FIG. 7 illustrates a fifth preferred embodiment of the present invention. As shown, removable peel away member 38 holds the sheath 24 in a closed position wrapped around the stent (not shown in FIG. 7). The peel away member is preferably made of the same material as the sheath, such as polyesters or polyethylenes. Elongated member 26 is attached to the peel away member and is pulled through the working channel 18 to remove the peel way member 38 from the sheath 24, thus releasing the sheath 24 from the cap 20 to deploy the stent into the body cavity. Preferably, the sheath 24 completely wraps around the stent. The sheath 24 can then be left in the body cavity after it is removed from the cap 20 and the stent.

A method of deploying the stent 22 within a body cavity comprises the following steps. The protective cap 20 is mounted on the distal end 12 of an endoscope 10 and the stent 22 is compressed circumferentially over the perimeter of the protective cap 20. The sheath 24 is releasably wrapped around the stent 22 to hold it in a compressed configuration over the protective cap 20. The sheath 24 has the flexible, elongated member 26 engaged with the sheath 24 extending through a working channel 18 of the endoscope 10. The endoscope is then inserted into a body cavity to the site of stent deployment. To deploy the stent 22, the flexible, elongated member 26 is withdrawn through the working channel 18 to release the sheath 24 from the cap 20, thereby causing the stent 22 to deploy. The order of these steps can be altered. For instance, the cap 20, the stent 22, and the sheath 24 may be assembled first, and then the assembly may be placed on to the distal end 12 of an endoscope.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for retaining and releasing a stent circumferentially compressed on a distal end of an endoscope, comprising:

a protective cap adapted for mounting on said distal end of said endoscope;

a sheath adapted to be releasably wrapped around said stent to hold said stent in compressed configuration over said protective cap; and a flexible, elongated member extending through a working channel of said endoscope and having one end attached to a release device for removing said sheath from said protective cap and for deploying said stent in a substantially linear transverse alignment within said body cavity by withdrawing said elongated member through the working channel of said endoscope.

2. The device according to claim 1, wherein said protective cap is adapted to be circumferentially attached to said distal end of the endoscope.

3. The device according to claim 1, wherein said release device comprises a ring with a flanged portion that engages said sheath for removably sliding said sheath over said protective cap.

4. The device according to claim 1, wherein said release device comprises concentric inner and outer rings, said inner ring attached to said flexible, elongated member, said rings being disposed over said protective cap with a portion of said sheath disposed between said rings to thereby maintain said sheath in place over said stent until said rings are withdrawn from said protective cap.

5. The device according to claim 4, wherein one end of said flexible, elongated member is disposed in a compressed relationship between said inner and outer rings.

6. The device according to claim 1, wherein said release device is a removable peel-away portion attached to said one end of said flexible, elongated member, said removable peel-away portion maintaining said sheath in a closed position.

7. The device according to claim 1, wherein said flexible, elongated member is a pull-wire extending through said working channel and exiting from said endoscope at said distal end.

8. A stent deployment device for deploying a stent within a body cavity used with an endoscope having a distal end and a working channel, the stent deployment device comprising:

a protective cap having a perimeter, the protective cap being mounted on said distal end of said endoscope;

a flexible stent circumferentially compressed over the perimeter of said cap;

a sheath releasably wrapped around said stent to hold said stent in compressed configuration over said protective cap; and a flexible, elongated member extending through the working channel of said endoscope and having one end attached to a release device for removing said sheath from said protective cap and deploying said stent in a substantially linear transverse alignment within said body cavity.

9. The stent deployment device according to claim 8, wherein said protective cap is circumferentially attached to said distal end of the endoscope.

10. The stent deployment device according to claim 8, wherein said release device comprises a ring with a flanged portion that engages said sheath for removably sliding said sheath over said protective cap.

11. The stent deployment device according to claim 8, wherein said release device comprises concentric inner and outer rings, said inner ring attached to said flexible, elongated member, said rings being disposed over said protective cap with a portion of said sheath disposed between said rings to thereby maintain said sheath in place over said stent until said rings are withdrawn from said protective cap.

12. The stent deployment device according to claim 11, wherein one end of said flexible, elongated member is disposed in a compressed relationship between sad inner and outer rings.

13. The stent deployment device according to claim 8, wherein said release device is a removable peel-away portion attached to said one end of said flexible, elongated member, said removable peel-away portion maintaining said sheath in a closed position.

14. The stent deployment device according to claim 8, wherein said flexible, elongated member is a pull-wire extending through said working channel and exiting from said endoscope at said distal end.

15. A method of deploying a stent within a body cavity, comprising the steps of:

mounting a protective cap on a distal end of an endoscope;

compressing a stent circumferentially over the perimeter of said protective cap;

releasably wrapping a sheath around said stent to hold said stent in a compressed configuration over said protective cap, said sheath having a flexible, elongated member engaged with said sheath extending through a working channel of said endoscope; and withdrawing said flexible, elongated member through said working channel of said endoscope to release said sheath from said cap, thereby causing said stent to deploy.

16. The method of claim 15, wherein said flexible, elongated member engages with said sheath by means of a release device for said sheath.

* * * * *